(12) United States Patent
Kuhrts

(10) Patent No.: US 9,731,015 B2
(45) Date of Patent: Aug. 15, 2017

(54) WATER-SOLUBLE LIPOPHILIC NATURAL COMPOUND FORMULATIONS

(71) Applicant: Eric Hauser Kuhrts, Novato, CA (US)

(72) Inventor: Eric Hauser Kuhrts, Novato, CA (US)

( * ) Notice: Subject to any disclaimer, the term of this patent is extended or adjusted under 35 U.S.C. 154(b) by 0 days.

(21) Appl. No.: 14/419,633

(22) PCT Filed: Aug. 5, 2013

(86) PCT No.: PCT/US2013/053585
§ 371 (c)(1),
(2) Date: Feb. 4, 2015

(87) PCT Pub. No.: WO2014/025672
PCT Pub. Date: Feb. 13, 2014

(65) Prior Publication Data
US 2015/0182625 A1  Jul. 2, 2015

Related U.S. Application Data

(60) Provisional application No. 61/679,703, filed on Aug. 4, 2012.

(51) Int. Cl.

| | | |
|---|---|---|
| *A61K 9/107* | (2006.01) | |
| *A61K 47/08* | (2006.01) | |
| *A61K 31/122* | (2006.01) | |
| *A61K 9/00* | (2006.01) | |
| *A61K 47/44* | (2017.01) | |
| *A61K 9/48* | (2006.01) | |
| *A61K 36/752* | (2006.01) | |
| *A61K 36/82* | (2006.01) | |
| *A61K 31/01* | (2006.01) | |
| *A61K 31/065* | (2006.01) | |
| *A61K 31/12* | (2006.01) | |
| *A61K 31/352* | (2006.01) | |
| *A61K 31/353* | (2006.01) | |
| *A23L 2/52* | (2006.01) | |
| *A61K 9/20* | (2006.01) | |
| *A61K 31/047* | (2006.01) | |
| *A61K 38/43* | (2006.01) | |

(52) U.S. Cl.
CPC ............... *A61K 47/08* (2013.01); *A23L 2/52* (2013.01); *A61K 9/0014* (2013.01); *A61K 9/0019* (2013.01); *A61K 9/0095* (2013.01); *A61K 9/1075* (2013.01); *A61K 9/2013* (2013.01); *A61K 9/48* (2013.01); *A61K 9/4858* (2013.01); *A61K 31/01* (2013.01); *A61K 31/047* (2013.01); *A61K 31/065* (2013.01); *A61K 31/12* (2013.01); *A61K 31/122* (2013.01); *A61K 31/352* (2013.01); *A61K 31/353* (2013.01); *A61K 36/752* (2013.01); *A61K 36/82* (2013.01); *A61K 38/43* (2013.01); *A61K 47/44* (2013.01); *A23V 2002/00* (2013.01)

(58) Field of Classification Search
CPC ...................... A61K 9/1075; A61K 31/122
See application file for complete search history.

(56) References Cited

U.S. PATENT DOCUMENTS

| | | | |
|---|---|---|---|
| 6,441,050 B1 * | 8/2002 | Chopra ............... | A61K 9/0095 424/439 |
| 2010/0247632 A1 | 9/2010 | Dong et al. | |
| 2011/0054029 A1 | 3/2011 | Kuhrts | |
| 2011/0281957 A1 | 11/2011 | Kuhrts | |

FOREIGN PATENT DOCUMENTS

| WO | WO 2008/101344 A1 | 8/2008 |
|---|---|---|
| WO | WO 2012/054090 A1 | 4/2012 |

OTHER PUBLICATIONS

PCT Application No. PCT/US2013/053585: Filing date Aug. 5, 2013; Kuhrts Hauser Eric; International Search Report mailed Dec. 12, 2013.

* cited by examiner

*Primary Examiner* — Rosanne Kosson
(74) *Attorney, Agent, or Firm* — Thorpe North & Western

(57) ABSTRACT

Methods and formulations for increasing the water solubility and/or bioavailability of a lipophilic natural compounds is disclosed. The formulations may be employed to make liquid filled capsules or clear and stable beverages containing therapeutic amounts of the active ingredients, for example.

23 Claims, No Drawings

WATER-SOLUBLE LIPOPHILIC NATURAL COMPOUND FORMULATIONS

BACKGROUND AND FIELD OF THE INVENTION

Flavonoids are abundant throughout nature and exert a broad range of biological activities in plants and animals. There are now considered to be over 4,000 flavonoids existent in nature. These compounds are the primary source for the colors that occur in the fall in many flowers and trees. Flavonoids are found in fruits, vegetables, nuts, seeds, herbs, spices, stems, flowers, red wine, cocoa, and tea, and are consumed on a regular basis in the human diet. These compounds can be classified according to their substituents into flavanols, anthocyanidins, flavones, flavanones, and chalcones. Some of the biological activities of flavonoids include anti-inflammatory, antiviral, antifungal, antibacterial, estrogenic, anti-oxidant, antiallargenic, anticarcinogenic, antithrombotic, hepatoprotective, and antiproliferative.

Some of the principle flavonoids that have been studied and found to have potential as therapeutic agents include flavonoids or flavanols from green tea and cocoa (or dark chocolate) such as epigallocatechin gallate, epigallocatechin, epicatechin, catechin, and epicatechin gallate, flavonoids from grape-type fruits or berries such as resveratrol (3,5,4'-trihydroxystilbene), pterostilbene derived from natural sources such as blueberries, grapes, and other berries, or other botanical sources. They can also be produced synthetically as 98% pterostilbene, compounds from soy, such as genistein and diadzein, and quercetin, the richest source of which is onions. Pterostilbene, or 3,5-Dimethoxy-4-stilbenol or dimethoxyresveratrol (CAS#537-42-8), has a molecular weight of 256.299, and is also a lipophilic compound, making it insoluble in water. Pterostilbene has different pharmacokinetic properties due to differences in the way it is metabolized compared to resveratrol, and therefore has a longer half-life (stays in the blood-steam longer).

Other natural compounds found to be beneficial for health include lutein (extracted from marigold flowers, lycopene (extracted from tomatoes), curcumin (for example 1,7-Bis (4-hydroxy-3-methoxyphenyl)-1,6-heptadiene-3,5-dione, 99% by HPLC), turmeric, co-enzyme Q-10 (ubidecarenone, ubiquinone, ubiquinol), epigallocatechin gallate (EGCG) derived from green tea, (−)-epicatechin from cocoa powder, essential oils such as citrus essential oils, grapefruit seed extracts, D-limonene, and other lipophilic flavor essential oils or natural compounds, carotenoids, astaxanthin, and phosphatidylserine. These lipophilic compounds can be classified as nutraceutical compounds or natural flavor essences because they are derived from nature and can be used therapeutically. These compounds typically will not soluble in water, and tend to float on water, and will not form a stable water soluble solution that is crystal clear and remains that way over time.

In order for any therapeutic molecular substance to be transported through the gastrointestinal tract, enter the blood, and eventually reach the organs and cells inside the body, the molecule should be finely dispersible or dissolvable in the aqueous phase of the intestinal fluid. Without dissolution, the drug will typically pass through the GI-tract. Flavonoids such as resveratrol are virtually insoluble in water, and animal pharmacokinetic studies of oral doses have demonstrated very low bioavailability. Likewise, human studies with green tea extracts standardized to the active catechins, have demonstrated very low absorption, usually less than 1% of the oral dose in animal or human studies. In fact, in one study, plasma tea catechin concentrations determined in humans after oral consumption of a green tea extract were 5-50 times less than the concentrations shown to exert biological activities in in vitro systems. Animal pharmacokinetic studies with trans-resveratrol also indicate less than 1-2% in plasma after an oral dose. No quercetin could be found in plasma after oral administration of up to 4 g in humans. Many flavonoids are lipophilic or fat soluble, and have very low solubility in water (hydrophobic). Only small amounts of resveratrol are contained in red wine. For example, resveratrol in wine may vary from 0.2 to 5.8 mg/liter. Co-enzyme Q-10 is a good example of a natural fat soluble compound that is hydrophobic, or insoluble in water and thus insoluble in water containing beverages such as juices or soft drinks.

Due to the many desirable properties of lipophilic natural compounds, it would be advantageous to have improved water soluble formulations and/or enhanced bioavailability formulations for dosing in vivo.

SUMMARY

A water-solubilized lipophilic natural compound formulation is disclosed. The formulation can include a lipophilic natural compound selected from the group consisting of co-enzyme Q-10, pterostilbene, lutein, lycopene, essential flavor oils, grapefruit seed extract, green tea extract, epigallocatechin gallate, epigallocatechin, epicatechin, catechin, epicatechin gallate, genistein, diadzein, quercetin, curcumin, D-limonene, lemon oil, carotenoids, astaxanthin, phosphatidylserine, ethyl pyruvate, esters thereof, salts thereof, metabolites thereof, prodrugs thereof, and mixtures thereof. The lipophilic natural compound c present at a concentration of at least 20% by weight. The formulation can also include a non-ionic surfactant and water. In another example, a method for enhancing the bioavailability of a lipophilic natural compound in a subject can include administering to the subject a therapeutically effective amount of the water-solubilized lipophilic natural compound described above.

DETAILED DESCRIPTION

In describing and claiming the present disclosure, the following terminology will be used.

The singular forms "a," "an," and "the" include plural referents unless the context clearly dictates otherwise. Thus, for example, reference to "a non-ionic surfactant" includes reference to one or more of such compounds.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

The term "pharmaceutically acceptable salts" or "salts" is meant to include salts of the active compounds which are prepared with relatively nontoxic acids or bases, depending on the particular substituent moieties found on the compounds described herein. When formulations of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When formulations of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific formulations of the present disclosure contain both basic and acidic functionalities that allow the compounds to be converted into either base or acid addition salts. The neutral forms of the compounds are typically regenerated by contacting the salt with a base or acid and isolating the parent compound in the conventional manner. The parent form of the compound differs from the various salt forms in certain physical properties, such as solubility in polar solvents.

In addition to salt forms, the present disclosure provides compounds, which are in a prodrug form, metabolites, esters, or the like.

"Prodrugs" of the compounds described herein are those compounds that readily undergo chemical changes under physiological conditions to provide the formulations of the present disclosure. Additionally, prodrugs can be converted to the formulations of the present disclosure by chemical or biochemical methods in an ex vivo environment. For example, prodrugs can be slowly converted to the formulations of the present disclosure when placed in a transdermal patch reservoir with a suitable enzyme or chemical reagent.

Certain formulations of the present disclosure can exist in unsolvated forms as well as solvated forms, including hydrated forms. In general, the solvated forms are equivalent to unsolvated forms and are encompassed within the scope of the present disclosure. Certain formulations of the present disclosure may exist in multiple crystalline or amorphous forms. In general, all physical forms are equivalent for the uses contemplated by the present disclosure and are intended to be within the scope of the present disclosure.

Certain formulations of the present disclosure possess asymmetric carbon atoms (optical centers) or double bonds. The racemates, diastereomers, tautomers, geometric isomers and individual isomers are encompassed within the scope of the present disclosure. The formulations of the present disclosure do not include those which are known in the art to be too unstable to synthesize and/or isolate.

The formulations of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the formulations of the present disclosure, whether radioactive or not, are encompassed within the scope of the present disclosure.

"Nutraceutical," as used herein, includes lipophilic compounds or essential oils derived from natural sources such as blueberries, grapes, and other berries, soybeans, cocoa beans, tomatoes, green tea, turmeric, citrus fruit, or other botanical sources, or produced synthetically as high purity compounds of identical chemical structure to the naturally derived sources, or produced through fermentation. Lipophilic natural compounds include co-enzyme Q-10, pterostilbene, lutein, lycopene, essential flavor oils such as citrus oil, grapefruit seed extract, green tea extract, EGCG, cocoa extract, epigallocatechin gallate, epigallocatechin, epicatechin, catechin, epicatechin gallate, quercetin, curcumin, D-limonene, lemon oil, carotenoids, astaxanthin, ethyl pyruvate, phosphatidylserine, etc.

It is also noted that any of the formulations described herein can be used in the context of "combination therapy" or "adjunct therapy" with other drugs to treat or otherwise provide a benefit with respect to a disease or other malady. This combination therapy can be sequential therapy where the patient is treated first with one drug and then the other or the two drugs are given simultaneously. The present disclosure includes combination therapy or adjunct therapy using the water soluble formulations of the present disclosure.

"Subject" or "Patient" refers to a mammalian subject, including human.

As used herein, the term "clear" as it relates to a solution or aqueous solution refers to a solution containing the natural lipophilic compound in a water containing solution (e.g. a beverage) that is free of visible particles of undissolved compound. The clear solution or clear aqueous solution is defined include both solutions as well as very fine dispersions, as long as the solution appears to remain clear upon sitting undisturbed for 1 hour or more. Essentially, no visible (to the naked eye) particles or micelles are present. Where the clear aqueous solution is a beverage, the clear aqueous solution may sometimes not need to be shaken prior to consuming.

It has been recognized that non-ionic surfactants may be used to increase the solubility and/or bioavailability of nutraceutical lipophilic compounds, including many esters, salts (e.g. a pharmaceutically acceptable salt), prodrugs, or metabolites thereof. Thus, non-ionic surfactants may be used to form water-soluble formulations containing the lipophilic natural compound.

In one aspect, the present disclosure provides a water-soluble lipophilic natural compound formulation including a natural lipophilic compound and a non-ionic surfactant. In another aspect, the formulation can be a water-solubilized lipophilic natural compound which also includes water. In either case, the natural lipophilic compound can be selected from the group consisting of co-enzyme Q-10, pterostilbene, lutein, lycopene, essential flavor oils, grapefruit seed extract, green tea extract, EGCG, epigallocatechin gallate, epigallocatechin, epicatechin, catechin, epicatechin gallate, genistein, diadzein, quercetin, curcumin, D-limonene, lemon oil, carotenoids, astaxanthin, phosphatidylserine, ethyl pyruvate, esters thereof, salts thereof, metabolites thereof, prodrugs thereof, and mixtures thereof.

In some embodiments, the water soluble formulation does not include a vegetable oil suspension or visible macromicelles (micelles visible to the naked eye) in water. In other embodiments, the water soluble formulation does not include an alcohol (e.g. the compound is not first dissolved in alcohol and then added to water). In another aspect, the free form of the compound is preferred due to a higher concentration of the active compound.

The non-ionic surfactant can be a surface active agent that tends to be non-ionized (i.e. uncharged) in neutral solutions (e.g. neutral aqueous solutions). Useful non-ionic surfactants include, for example, non-ionic water soluble mono-, di-, and tri-glycerides; non-ionic water soluble mono- and di-fatty acid esters of polyethyelene glycol; non-ionic water soluble sorbitan fatty acid esters (e.g. sorbitan monooleates such as SPAN 80 and TWEEN 20 (polyoxyethylene 20 sorbitan monooleate)); polyglycolyzed glycerides; non-ionic water soluble triblock copolymers (e.g. poly(ethyleneoxide)/poly-(propyleneoxide)/poly(ethyleneoxide) triblock copolymers such as POLOXAMER 406 (PLURONIC F-127), and derivatives thereof.

Examples of non-ionic water soluble mono-, di-, and tri-glycerides include propylene glycol dicarpylate/dicaprate (e.g. MIGLYOL 840), medium chain mono- and diglycerides (e.g. CAPMUL and IMWITOR 72), medium-chain triglycerides (e.g. caprylic and capric triglycerides such as LAVRAFAC, MIGLYOL 810 or 812, CRODAMOL GTCC-PN, and SOFTISON 378), long chain monoglycerides (e.g. glyceryl monooleates such as PECEOL, and glyceryl monolinoleates such as MAISINE), polyoxyl castor oil (e.g. macrogolglycerol ricinoleate, macrogolglycerol hydroxystearate, macrogol cetostearyl ether), and derivatives thereof.

Non-ionic water soluble mono- and di-fatty acid esters of polyethyelene glycol include d-α-tocopheryl polyethyleneglycol 1000 succinate (TPGS), poyethyleneglycol 660 12-hydroxystearate (SOLUTOL HS 15), polyoxyl oleate and stearate (e.g. PEG 400 monostearate and PEG 1750 monostearate), and derivatives thereof.

Polyglycolyzed glycerides include polyoxyethylated oleic glycerides, polyoxyethylated linoleic glycerides, polyoxyethylated caprylic/capric glycerides, and derivatives thereof. Specific examples include LABRAFIL M-1944CS, LABRAFIL M-2125CS, LABRASOL, SOFTIGEN, and GELUCIRE.

In some embodiments, the non-ionic surfactant is a polyoxyl castor oil, or derivative thereof. Effective polyoxyl castor oils may be synthesized by reacting either castor oil or hydrogenated castor oil with varying amounts of ethylene oxide. Macrogolglycerol ricinoleate is a mixture of 83% relatively hydrophobic and 17% relatively hydrophilic components. The major component of the relatively hydrophobic portion is glycerol polyethylene glycol ricinoleate, and the major components of the relatively hydrophilic portion are polyethylene glycols and glycerol ethoxylates. Macrogolglycerol hydroxystearate is a mixture of approximately 75% relatively hydrophobic of which a major portion is glycerol polyethylene glycol 12-oxystearate.

In some embodiments, the water soluble formulations includes the natural lipophilic compound, metabolite, ester, prodrug, or salt thereof, and polyoxyl castor oil to form a transparent water soluble formulation. A "transparent water soluble formulation," as disclosed herein, refers to a formulation that can be clearly seen through with the naked eye and is optionally colored. In some embodiments, the transparent water soluble formulations do not contain particles (e.g. particles of undissolved lipophilic compound) visible to the naked eye. In certain embodiments, light may be transmitted through the transparent water soluble formulations without diffusion or scattering. Thus, in some embodiments, the transparent water soluble formulations are not opaque, cloudy or milky-white. Transparent water soluble formulations disclosed herein do not include milky-white emulsions or suspensions in vegetable oil such as corn oil. Transparent water soluble formulations are also typically not formed by first dissolving the compound in alcohol, and then mixed with water.

In some embodiments, the water soluble formulation is a non-alcoholic formulation. A "non-alcoholic" formulation, as used herein, is a formulation that does not include (or includes only in trace amounts) methanol, ethanol, propanol or butanol. In other embodiments, the formulation does not include (or includes only in trace amounts) ethanol.

The formulation can also be a non-aprotic solvated formulation. The term "non-aprotic solvated," as used herein, means that water soluble aprotic solvents are absent or are included only in trace amounts. Water soluble aprotic solvents are water soluble non-surfactant solvents in which the hydrogen atoms are not bonded to an oxygen or nitrogen and therefore cannot donate a hydrogen bond.

In some embodiments, the water soluble formulation does not include (or includes only in trace amounts) a polar aprotic solvent. Polar aprotic solvents are aprotic solvents whose molecules exhibit a molecular dipole moment but whose hydrogen atoms are not bonded to an oxygen or nitrogen atom. Examples of polar aprotic solvents include aldehydes, ketones, dimethyl sulfoxide (DMSO), and dimethyl formamide (DMF). In other embodiments, the water soluble formulation does not include (or includes only in trace amounts) dimethyl sulfoxide. Thus, in some embodiments, the water soluble formulation does not include DMSO. In a related embodiment, the water soluble formulation does not include DMSO or ethanol.

In still other embodiments, the water soluble formulation does not include (or includes only in trace amounts) a non-polar aprotic solvent. Non-polar aprotic solvents are aprotic solvents whose molecules exhibit a molecular dipole of approximately zero. Examples include hydrocarbons, such as alkanes, alkenes, and alkynes.

The water soluble formulation of the present disclosure includes formulations dissolved in water (i.e. aqueous formulations), as well as formulations without water that are suitable for soft-gelatin capsules, that can form soluble solutions in gastric fluid after ingestion. In most embodiments, the water soluble formulation forms a transparent water soluble formulation when added to water.

In some embodiments, the water soluble formulation consists essentially of the lipophilic natural compound, ester, metabolite, prodrug, or salt thereof, and a non-ionic surfactant. Where a water soluble formulation "consists essentially of" the lipophilic natural compound and a non-ionic surfactant, the formulation includes the lipophilic natural compound and the non-ionic surfactant, and optionally additional components widely known in the art to be useful in neutraceutical formulations, such as preservatives, excipients, pH modifiers, taste enhancers, buffers, water, etc. As a specific example, a water soluble formulation that "consists essentially of" the natural lipophilic compound (e.g. lutein, a lutein metabolite, ester, or salt thereof) does not include any significant formulation additive or component that would materially affect the basic and novel properties of the disclosure.

As also mentioned, in some embodiments, the water soluble formulation is a water solubilized formulation. A "water-solubilized" formulation, as used herein, includes the natural lipophilic compound, esters, metabolites, prodrugs, or salt thereof, a non-ionic surfactant, and water (e.g. a water containing liquid), but often does not include organic solvents (e.g. ethanol). In some embodiments, the water solubilized formulation is a transparent water soluble formulation.

In another aspect, the present disclosure provides a method for enhancing the bioavailability of the lipophilic natural compounds in a subject. The method includes combining the lipophilic natural compound, metabolite or salt thereof, and a non-ionic surfactant to form a surfactant-lipophilic compound mixture. The surfactant-lipophilic compound mixture may be administered to the subject thereby enhancing the bioavailability of the compound or metabolite of the compound. The bioavailability is enhanced compared to the bioavailability of the compound in the absence of non-ionic surfactant.

A subject is an organism that is treated using one of the methods of the present disclosure. In some embodiment, the subject is a mammalian subject, such as a human or domestic animal.

In another aspect, the present disclosure provides a method of dissolving the lipophilic natural compound, a lipophilic natural compound metabolite or salt thereof in water. The method includes combining the lipophilic natural compound with a non-ionic surfactant that has been warmed to a temperature of at least 90-200° F., to form a surfactant-lipophilic natural compound mixture. The surfactant-lipophilic natural compound mixture is combined with water that has been warmed to at least 90-200° F., thereby dissolving the compound in water. If the formulation is for inclusion in a soft-gelatin capsule, the warm lipophilic natural compound and surfactant can be combined with other oils, such as soybean oil or olive oil, and filled into the capsules without water. The heating temperature is typically selected to avoid chemical breakdown of the lipophilic natural compound and/or non-ionic surfactant. This temperature is usually in the range of 90-150° F., but usually is in the range of 100-125° F. In some embodiments, the resulting solution is a water soluble formulation or transparent water soluble formulation as described above. For example, the resulting solution may be a water soluble formulation that is a crystal clear solution, with no particles visible to the naked eye. An effective amount of the water soluble formulation of the present disclosure is an amount sufficient to achieve the intended purpose of a method of the present disclosure, such as treating a particular disease state in a subject (e.g. a human subject).

The amount of lipophilic natural compound adequate to treat a disease (e.g. through modulation of VEGF, COX, cell proliferation), is defined as a "therapeutically effective" dose. The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the rate of absorption, bioavailability, metabolism, clearance, and the like (for example, the latest Remington's, supra). The state of the art allows the clinician to determine the dosage regimen for each individual patient and disease or condition treated.

Single or multiple administrations of lipophilic natural compound formulations can be administered depending on the dosage and frequency as desired and tolerated by the patient. The formulations should provide a sufficient quantity of active agent to effectively treat the disease state. Lower dosages can be used, particularly when the drug is administered to an anatomically secluded site in contrast to administration orally, into the blood stream, into a body cavity or into a lumen of an organ. Substantially higher dosages can be used in topical administration. Actual methods for preparing parenterally administrable lipophilic natural compound formulations will be known or apparent to those skilled in the art.

In some embodiments, the lipophilic natural compound is present in the water soluble formulation at a concentration of at least 1%, 5%, 10%, 20%, 25%, 30%, 35%, 45%, 45%, or 50% by weight. In other embodiments the compounds is present in the water soluble formulation at a concentration from 0.01%, 0.1%, 1% to 80%, 5% to 50%, 10% to 35%, or 20% to 25% (by weight). The compound may also be present (e.g. in a beverage formulation) at a concentration from 0.5 to 250 mg per 3.3 fluid oz, or around 2-10 mg per ml. In other embodiments, the compound is present at a concentration from 0.01 mg/ml to 50 mg/ml. There is a maximum concentration for achieving a crystal clear solution. Concentrations of the compound above 20% using polyoxyl 40 castor oil (i.e. macrogoglycerol hydroxystearate) as the surfactant will no longer result in a crystal-clear solution in water. Therefore, the concentration range would be from 0.1% to 30% in the surfactant, or 0.01 to 20 mg/ml for the lipophilic natural compound, with the preferred concentration around 20 mg/ml, depending on the compound. This represents a ratio of the lipophilic natural compound to surfactant of 1:5 to 1:10. In some concentrated formulations (e.g. a soft gel capsule formulation), compound may be present at about 1 to 50 mg/ml, or around 20 mg/ml, or at least 1 mg/ml.

In other embodiments, at least 0.5 mg, 1 mg, 2 mg, 3 mg, 4 mg, 5 mg, 10 mg, 20 mg, 30 mg, 40 mg, 50 mg, 100 mg, 200 mg, 300 mg, 400 mg, 500 mg, or 1 g of the compound is present in the water soluble beverage formulation. In other embodiments, 0.1 mg to 2 g, 0.5 mg to 1 g, 1 mg to 500 mg, 1 mg to 100 mg, 1 mg to 50 mg, 1 mg to 10 mg, or 1 mg to 5 mg of lipophilic natural compound is present in the water soluble beverage formulation.

In some embodiments, the water soluble formulation is in the form of a pharmaceutical composition. The pharmaceutical composition may include the lipophilic natural compound, metabolite, a non-ionic surfactant, and a pharmaceutically acceptable excipient. After a pharmaceutical composition including the lipophilic natural compound of the disclosure has been formulated in an acceptable carrier, it can be placed in an appropriate container and labeled for treatment of an indicated condition. For administration of the compound, such labeling would include, e.g., instructions concerning the amount, frequency and method of administration.

Any appropriate dosage form is useful for administration of the water soluble formulation of the present disclosure, such as oral, parenteral and topical dosage forms. Oral preparations include tablets, pills, powder, dragees, capsules (e.g. soft-gel capsules), liquids, lozenges, gels, syrups, slurries, beverages, suspensions, etc., suitable for ingestion by the patient. The formulations of the present disclosure can also be administered by injection, that is, intravenously, intramuscularly, intracutaneously, subcutaneously, intraduodenally, or intraperitoneally. Also, the formulations described herein can be administered by inhalation, for example, intranasally. Additionally, the formulations of the present disclosure can be administered transdermally. The formulations can also be administered by in intraocular, intravaginal, and intrarectal routes including suppositories, insufflation, powders and aerosol formulations. Thus, the formulations described herein may be adapted for oral administration.

For preparing pharmaceutical compositions from the formulations of the present disclosure, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature.

Suitable carriers include magnesium carbonate, magnesium stearate, talc, sugar, lactose, pectin, dextrin, starch (from corn, wheat, rice, potato, or other plants), gelatin, tragacanth, a low melting wax, cocoa butter, sucrose, mannitol, sorbitol, cellulose (such as methyl cellulose, hydroxypropylmethyl-cellulose, or sodium carboxymethylcellulose), and gums (including arabic and tragacanth), as well as proteins such as gelatin and collagen. If desired, disintegrating or co-solubilizing agents may be added, such as the cross-linked polyvinyl pyrrolidone, agar, alginic acid, or a salt thereof, such as sodium alginate. In powders, the carrier is a finely divided solid, which is in a mixture with the finely divided active component. In tablets, the active component is mixed with the carrier having the necessary binding properties in suitable proportions and compacted in the shape and size desired.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the disclosure can also be used orally using, for example, push-fit capsules made of gelatin, as well as soft, sealed capsules made of gelatin and a coating such as glycerol or sorbitol. Push-fit capsules can contain the lipophilic natural compound mixed with a filler or binders such as lactose or starches, lubricants such as talc or magnesium stearate, and, optionally, stabilizers. In soft capsules, the compound may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, beverages, and emulsions, for example, water or water/propylene glycol solutions. For parenteral injection, liquid preparations can be formulated in solution in aqueous polyethylene glycol solution.

Aqueous solutions and beverages suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the lipophilic natural compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. The formulations of the disclosure can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The formulations of the disclosure can be delivered transdermally, by a topical route, formulated as applicator sticks, solutions, suspensions, emulsions, gels, creams, ointments, pastes, jellies, paints, powders, and aerosols. A water soluble formulation as described herein may be sprayed directly onto the skin.

The formulations can also be delivered as microspheres for slow release in the body. For example, microspheres can be administered via intradermal injection of drug-containing microspheres, which slowly release subcutaneously, or, as microspheres for oral administration. Both transdermal and intradermal routes afford constant delivery for weeks or months.

The formulations of the disclosure can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the formulations of the disclosure are useful for parenteral administration, such as intravenous (IV) administration or administration into a body cavity or lumen of an organ. The formulations for administration will commonly comprise a solution of lipophilic natural compound dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as desired to approximate physiological conditions such as pH adjusting and buffering agents, toxicity adjusting agents, e.g., sodium acetate, sodium chloride, potassium chloride, calcium chloride, sodium lactate and the like. The concentration of lipophilic natural compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the disclosure can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the lipophilic natural compound, metabolite or ester thereof into the target cells in vivo.

The formulations may be administered as a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted according to the particular application and the potency of the active component. The composition can, if desired, also contain other compatible therapeutic agents.

Subject non-ionic surfactants may be assayed for their ability to solubilize the lipophilic natural compound, or metabolite of the compound using any appropriate method. Typically, a heated, non-ionic surfactant is contacted with the lipophilic natural compound and mixed mechanically and/or automatically using a shaker or heated mixing vessel device. Warm water may be optionally added, for example, where the compound and/or surfactant is in powder form. The solution is typically heated to a temperature of at least 90-200° F. The heating temperature is selected to avoid chemical breakdown of the lipophilic natural compound or lipophilic natural compound metabolite and non-ionic surfactant.

The resulting solution may be visually inspected for colloidal particles to determine the degree of solubility of the compound. Alternatively, the solution may be filtered and analyzed to determine the degree of solubility. For example, a spectrophotometer may be used to determine the concentration of the compound present in the filtered solution. Typically, the test solution is compared to a positive control containing a series of known quantities of pre-filtered lipophilic natural compound solutions to obtain a standard concentration versus UV/vis absorbance curve. Alternatively, high performance liquid chromatography may be used to determine the amount of the compound in solution.

High throughput solubility assay methods are well known in the art. Typically, these methods involve automated dispensing and mixing of solutions with varying amounts of non-ionic surfactants, lipophilic natural compound, and optionally other co-solvents. The resulting solutions may then be analyzed to determine the degree of solubility using any appropriate method as discussed above.

For example, the Millipore MultiScreen Solubility filter Plate® with modified track-etched polycarbonate, 0.4 μm membrane is a single-use, 96-well product assembly that includes a filter plate and a cover. The device is intended for processing aqueous solubility samples in the 100-300 μL volume range. The vacuum filtration design is compatible with standard, microtiter plate vacuum manifolds. The plate is also designed to fit with a standard, 96-well microtiter receiver plate for use in filtrate collection. The MultiScreen Solubility filter Plate® has been developed and QC tested for consistent filtration flow-time (using standard vacuum), low aqueous extractable compounds, high sample filtrate recovery, and its ability to incubate samples as desired to perform solubility assays. The low-binding membrane has been specifically developed for high recovery of dissolved organic compounds in aqueous media.

The aqueous solubility assay allows for the determination of lipophilic natural compound solubility by mixing, incubating and filtering a solution in the MultiScreen Solubility filter plate. After the filtrate is transferred into a 96-well collection plate using vacuum filtration, it is analyzed by UV/Vis spectroscopy to determine solubility. Additionally, LC/MS or HPLC can be used to determine compound solubility, especially for compounds with low UV/Vis absorbance and/or compounds with lower purity. For quantification of aqueous solubility, a standard calibration curve may be determined and analyzed for each compound prior to determining aqueous solubility.

Test solutions may be prepared by adding an aliquot of concentrated drug or compound. The solutions are mixed in a covered 96-well MultiScreen Solubility filter plate for 1.5 hours at room temperature. The solutions are then vacuum filtered into a 96-well, polypropylene, V-bottomed collection plate to remove any insoluble precipitates. Upon complete filtration, 160 μL/well are transferred from the collection plate to a 96-well UV analysis plate and diluted with 40 μL/well of acetonitrile. The UV/vis analysis plate is scanned from 260-500 nm with a UV/vis microplate spectrometer to determine the absorbance profile of the test compound.

Thus, one skilled in the art may assay a wide variety of non-ionic surfactants to determine their ability to solubilize lipophilic natural compounds.

The terms and expressions which have been employed herein are used as terms of description and not of limitation, and there is no intention in the use of such terms and expressions of excluding equivalents of the features shown and described, or portions thereof, it being recognized that various modifications are possible within the scope of the disclosure claimed. Moreover, any one or more features of any embodiment of the disclosure may be combined with any one or more other features of any other embodiment of the disclosure, without departing from the scope of the disclosure. For example, the features of the formulations are equally applicable to the methods of treating disease states described herein. All publications, patents, and patent applications cited herein are hereby incorporated by reference in their entirety for all purposes.

EXAMPLES

The following examples below are meant to illustrate certain embodiments of the present disclosure, and are not intended to limit the scope of the disclosure.

Example 1

Water soluble compositions of co-enzyme Q-10 were formulated containing the non-ionic surfactant macrogolglycerol hydroxystearate (polyoxyl 40 castor oil). The polyoxyl castor oil (non-ionic surfactant) was heated and stirred to a temperature of about 100° F., then the powdered co-enzyme Q-10 (Co-Q-10) was added slowly and mixed until a clear viscous emulsion phase formulation was formed containing dissolved Co-Q-10. The emulsion phase formulation included macrogolglycerol hydroxystearate 40 and powdered Co-Q-10. The Co-Q-10/surfactant mixture was then slowly added to warm water (100° F.) until a crystal clear solution was formed. The formulation also included other pH modifiers, preservatives, etc., in minor amounts. Table 1 below sets forth the formulation.

TABLE 1

| Co-Q-10 WS | |
|---|---|
| Ingredients | Wt % |
| Co-Enzyme Q-10 | 5.25% |
| Water | 64.25% |
| Macrogolglycerol hydroxystearate 40 | 30.20% |
| Sodium Benzoate | 0.06% |
| Potassium Sorbate | 0.04% |
| Citric Acid | 0.20% |
| Total | 100.00% |

The aqueous Co-Enzyme A-10 formulation was analyzed by HPLC and found to contain 0.5%, or 50 mg/ml co-enzyme Q-10 (ubidecarenone).

Example 2

A water soluble formulation of lycopene was prepared by mixing a lycopene extract (Lyc-O-Mato, Lycored corporation) containing 15% lycopene with polyoxyl castor oil. First, the polyoxyl castor oil was warmed about 100-110° F. and mixed with the liquid lycopene formulation until a clear red emulsion was formed. This emulsion was then very slowly added to water that has been heated to about 100-110° F. until a clear water soluble lycopene concentrate was obtained. The formulation also included other pH modifiers, preservatives, etc., in minor amounts. The water soluble concentrate was a deep red color and was added to additional water at room temperature to make a water soluble beverage. Table 2 below sets forth the formulation.

TABLE 2

| Lycopene WS | |
|---|---|
| Ingredients | Wt % |
| Lycopene | 3.3% |
| Water | 66.2% |
| Macrogolglycerol hydroxystearate 40 | 30.20% |
| Sodium Benzoate | 0.06% |
| Potassium Sorbate | 0.04% |
| Citric Acid | 0.20% |
| Total | 100.00% |

Example 3

A water soluble formulation of lutein was prepared by mixing a lutein extract (Xangold, Cognis Corporation) containing 80% lutein with polyoxyl castor oil. First, the polyoxyl castor oil was warmed to about 100-110° F. and then mixed with a powdered lutein formulation until a clear red emulsion was formed. This emulsion was then very slowly added to water that has been heated to about 100-110° F. until a clear water soluble lutein concentrate was obtained. The water soluble concentrate was a deep yellow/orange color and was added to additional water at room temperature to make a water soluble beverage. The formulation also included other pH modifiers, preservatives, etc., in minor amounts. Table 3 below sets forth the formulation.

TABLE 3

| Lutein WS | |
|---|---|
| Ingredients | Wt % |
| Lutein | 3.3% |
| Water | 66.2% |
| Macrogolglycerol hydroxystearate 40 | 30.20% |
| Sodium Benzoate | 0.06% |
| Potassium Sorbate | 0.04% |
| Citric Acid | 0.20% |
| Total | 100.00% |

Example 4

A water soluble formulation of quercetin was prepared with quercetin dihydrate. First, polyoxyl castor oil was heated to about 100-110° F. and stirred. The powdered quercetin dehydrate was added until a clear, slightly yellow emulsion was formed. This emulsion was then very slowly added to water that has been heated to about 100-110° F. until a clear water soluble quercetin concentrate was obtained. The water soluble concentrate was clear and free of visible particles, and was added to additional water at room temperature to make a clear water soluble beverage. The formulation also included other pH modifiers, preservatives, etc., in minor amounts. Table 4 below sets forth the formulation.

TABLE 4

| Quercetin WS | |
| --- | --- |
| Ingredients | Wt % |
| Quercetin dihydrate | 1.4% |
| Water | 68.1% |
| Macrogolglycerol hydroxystearate 40 | 30.20% |
| Sodium Benzoate | 0.06% |
| Potassium Sorbate | 0.04% |
| Citric Acid | 0.20% |
| Total | 100.00% |

Example 5

A water soluble formulation of a green tea extract containing EGCG was made by mixing a green tea extract containing 94% EGCG in warm polyoxyl castor (about 100-110° F.) until a clear emulsion was formed. This emulsion was then very slowly added to water that had been heated to about 100-110° F. until a clear water soluble EGCG green tea extract concentrate was obtained. The water soluble concentrate was added to additional water at room temperature to make a water soluble beverage. The formulation also included other pH modifiers, preservatives, etc., in minor amounts. Table 5 below sets forth the formulation.

TABLE 5

| EGCG Green Tea WS | |
| --- | --- |
| Ingredients | Wt % |
| EGCG 94% | 3.3% |
| Water | 66.2% |
| Macrogolglycerol hydroxystearate 40 | 30.20% |
| Sodium Benzoate | 0.06% |
| Potassium Sorbate | 0.04% |
| Citric Acid | 0.20% |
| Total | 100.00% |

Example 6

Water soluble compositions of lemon oil were formulated containing the non-ionic surfactant macrogolglycerol hydroxystearate (polyoxyl 40 castor oil). The polyoxyl castor oil (non-ionic surfactant) was heated and stirred to a temperature of about 100° F., then the lemon oil was added slowly and mixed until a clear viscous solution was formed containing dissolved lemon oil. The dissolved lemon oil emulsion was then slowly added to warm water (100° F.) until a crystal clear solution was formed. The water soluble concentrate was added to additional water at room temperature to make a crystal clear, water soluble beverage. The same formulation of example 6 was replicated with D-limonene. The formulation also included other pH modifiers, preservatives, etc., in minor amounts. Table 6 below sets forth the formulation.

TABLE 6

| Lemon Oil WS | |
| --- | --- |
| Ingredients | Wt % |
| Lemon Oil | 6.25% |
| Water | 65.25% |
| Macrogolglycerol hydroxystearate 40 | 30.20% |
| Sodium Benzoate | 0.06% |
| Potassium Sorbate | 0.04% |
| Citric Acid | 0.20% |
| Total | 100.00% |

Example 7

Water soluble compositions of grapefruit seed extract were formulated containing macrogolglycerol hydroxystearate (polyoxyl 40 castor oil). Grapefruit seed extract is a natural preservative and is effective against both gram positive and gram negative bacteria. The polyoxyl castor oil was heated and stirred to a temperature of about 100° F., and then the grapefruit seed oil was added slowly and mixed until a clear viscous solution was formed containing dissolved grapefruit seed extract. The dissolved grapefruit seed extract emulsion was then slowly added to warm water (100-110° F.) until a crystal clear solution was formed. The water soluble concentrate may be added to beverages or other emulsions to make a crystal clear, water soluble preservative system that is effective against both gram positive and gram negative bacteria. The formulation included pH modifiers, preservatives, etc., in minor amounts. Table 7 below sets forth the formulation.

TABLE 7

| Grapefruit seed WS | |
| --- | --- |
| Ingredients | Wt % |
| Grapefruit seed Extract | 2% |
| Water | 67.70% |
| Macrogolglycerol hydroxystearate 40 | 30% |
| Sodium Benzoate | 0.06% |
| Potassium Sorbate | 0.04% |
| Citric Acid | 0.20% |
| Total | 100.00% |

Example 8

Water soluble compositions of essential flavor oils were formulated containing macrogolglycerol hydroxystearate (polyoxyl 40 castor oil) and an essential flavor oil. Most essential oil flavors contain 20-45% alcohol to make them soluble. The polyoxyl castor oil (non-ionic surfactant) was heated and stirred to a temperature of about 100° F., and a pure orange essential oil containing no alcohol was slowly mixed with the polyoxyl castor oil until a clear viscous solution was formed containing dissolved essential orange oil. The orange essential oil emulsion was then slowly added to warm water (100-110° F.) until a crystal clear solution was formed. The water soluble concentrate can be added to beverages to impart flavor without the need of an alcohol containing essential oil extract. The formulation also included other pH modifiers, preservatives, etc., in minor amounts. Table 8 below sets forth the formulation.

TABLE 8

Orange Essential Oil WS

| Ingredients | Wt % |
|---|---|
| Orange Oil Flavor | 1.25% |
| Water | 68.25% |
| Macrogolglycerol hydroxystearate 40 | 30.20% |
| Sodium Benzoate | 0.06% |
| Potassium Sorbate | 0.04% |
| Citric Acid | 0.20% |
| Total | 100.00% |

Example 9

Water soluble compositions of curcumin were formulated containing macrogolglycerol hydroxystearate (polyoxyl 40 castor oil) and curcumin extract that is 99% pure 1,7-Bis (4-hydroxy-3-methoxyphenyl)-1,6-heptadiene-3,5-dione by HPLC. The polyoxyl castor oil (non-ionic surfactant) was heated and stirred to a temperature of about 125° F., and the curcumin powder was slowly mixed with the polyoxyl castor oil until a clear viscous solution was formed containing dissolved curcumin powder. The curcumin emulsion was then slowly added to warm water (100-125° F.) until a crystal clear solution was formed. The water soluble concentrate can be added to beverages to make a curcumin supplement.

The formulation also included other pH modifiers, preservatives, etc., in minor amounts. Table 9 below sets forth the formulation.

TABLE 9

Curcumin WS

| Ingredients | % in formula |
|---|---|
| Curcumin 99% | 1.25% |
| Water | 68.25% |
| Macrogolglycerol hydroxystearate 40 | 30.20% |
| Sodium Benzoate | 0.06% |
| Potassium Sorbate | 0.04% |
| Citric Acid | 0.20% |
| Total | 100.00% |

Example 10

A water soluble formulation of lutein is prepared by mixing a lutein extract (Xangold, Cognis Corporation) containing 80% lutein with polyoxyl castor oil. First, the polyoxyl castor oil is warmed to about 100-110° F. and then mixed with a powdered lutein formulation until a clear red emulsion is formed. This emulsion is then very slowly added to water that has been heated to about 100-110° F. until a clear water soluble lutein concentrate is obtained. The water soluble concentrate is a deep yellow/orange color and is added to additional water at room temperature to make a water soluble beverage. The formulation also can include other pH modifiers, preservatives, etc., in minor amounts. Table 10 below sets forth the formulation.

TABLE 10

Lutein WS

| Ingredients | Wt % |
|---|---|
| Lutein | 3.3% |
| Water | 86.4% |
| Macrogolglycerol hydroxystearate 40 | 10% |
| Sodium Benzoate | 0.06% |
| Potassium Sorbate | 0.04% |
| Citric Acid | 0.20% |
| Total | 100.00% |

Example 11

A water soluble formulation of lycopene is prepared by mixing a lycopene extract (Lyc-O-Mato, Lycored corporation) containing 15% lycopene with polyoxyl castor oil. First, the polyoxyl castor oil is warmed to about 100-110° F. and mixed with the liquid lycopene formulation until a clear red emulsion is formed. This emulsion is then very slowly added to water that is heated to about 100-110° F. until a clear water soluble lycopene concentrate is obtained. The formulation also may include other pH modifiers, preservatives, etc., in minor amounts. The water soluble concentrate is deep red color and can be added to additional water at room temperature to make a water soluble beverage. Table 11 below sets forth the formulation.

TABLE 11

Lycopene WS

| Ingredients | Wt % |
|---|---|
| Lycopene | 3.3% |
| Water | 56.4% |
| Macrogolglycerol hydroxystearate 40 | 40% |
| Sodium Benzoate | 0.06% |
| Potassium Sorbate | 0.04% |
| Citric Acid | 0.20% |
| Total | 100.00% |

What is claimed is:

1. A water-solubilized lipophilic natural compound formulation, comprising:
   a) a lipophilic natural compound selected from the group consisting of co-enzyme Q-10, pterostilbene, lutein, lycopene, essential flavor oils, grapefruit seed extract, green tea extract, epigallocatechin gallate, epigallocatechin, epicatechin, catechin, epicatechin gallate, genistein, diadzein, quercetin, curcumin, D-limonene, lemon oil, carotenoids, astaxanthin, phosphatidylserine, ethyl pyruvate, esters thereof, salts thereof, metabolites thereof, prodrugs thereof, and mixtures thereof, wherein said lipophilic natural compound is present at a concentration of at least 20% by weight;
   b) a non-ionic surfactant; and
   c) water.

2. The formulation of claim 1, wherein said formulation is a non-alcoholic formulation.

3. The formulation of claim 1, wherein said formulation is a non-aprotic solvated formulation.

4. The formulation of claim 1, wherein the formulation comprises at least 50 mg of the lipophilic natural compound.

5. The formulation of claim 1, wherein said non-ionic surfactant is a non-ionic water soluble mono-, di-, or tri-glyceride; non-ionic water soluble mono- or di-fatty acid ester of polyethyelene glycol; non-ionic water soluble sorbitan fatty acid ester; polyglycolyzed glyceride; non-ionic water soluble triblock copolymers; or derivative thereof.

6. The formulation of claim 1, wherein said non-ionic surfactant is a non-ionic water soluble mono-, di-, or tri-glyceride.

7. The formulation of claim 1, wherein said non-ionic surfactant is polyoxyl 40 castor oil.

8. The formulation of claim 1, wherein said non-ionic surfactant is macrogolglycerol ricinoleate or macrogolglycerol hydroxystearate.

9. The formulation of claim 1, wherein said non-ionic surfactant is macrogolglycerol hydroxystearate.

10. The formulation of claim 1, wherein said formulation is an oral formulation.

11. The formulation of claim 10, wherein said oral formulation is a soft gel capsule.

12. The formulation of claim 10, wherein said oral formulation is a tablet.

13. The formulation of claim 10, wherein said oral formulation is a beverage.

14. The formulation of claim 1, wherein said formulation is an injectable formulation.

15. The formulation of claim 1, wherein said formulation is a topical formulation.

16. The formulation of claim 1, further comprising a pharmaceutically acceptable excipient.

17. The formulation of claim 1, wherein the water is present at greater than 50 wt % and the formulation is clear with no visible particles or micelles to the naked eye.

18. A method for enhancing the bioavailability of a lipophilic natural compound in a subject, comprising:
    administering to the subject a therapeutically effective amount of the water-solubilized lipophilic natural compound formulation of claim 1.

19. The method of claim 18, wherein the formulation is in the form of a liquid consumable.

20. The method of claim 19, wherein the liquid consumable further comprises at least 50 wt % water and the lipophilic natural compound is solubilized or finely dispersed in the water to form a clear solution.

21. The method of claim 19, wherein the liquid consumable is contained with a soft gel tablet.

22. The method of claim 18, wherein the formulation is in the form of a solid consumable.

23. The method of claim 18, wherein the formulation is in the form of a topical or injectable formulation.

* * * * *